(12) United States Patent
Stingley et al.

(10) Patent No.: US 6,212,698 B1
(45) Date of Patent: Apr. 10, 2001

(54) URINE COLLECTION KIT

(76) Inventors: Beverly J. Stingley, 6501 N. Elmwood Ct., Kansas City, MO (US) 64119; Sandra S. Lowman, 504 Amesbury Dr., Smithville, MO (US) 64089

( * ) Notice: Subject to any disclaimer, the term of this patent is extended or adjusted under 35 U.S.C. 154(b) by 0 days.

(21) Appl. No.: 09/550,893

(22) Filed: Apr. 17, 2000

(51) Int. Cl.[7] .................................................. E03D 9/10
(52) U.S. Cl. ................................... 4/315; 4/144.1; 4/341; 600/573
(58) Field of Search ............................... 4/301, 315, 340, 4/341, 342, 144.1; 600/573, 574, 580

(56) References Cited

U.S. PATENT DOCUMENTS

| | | |
|---|---|---|
| D. 244,403 | 5/1977 | DeAngelis . |
| D. 275,606 | 9/1984 | Zawachi . |
| D. 290,880 | 7/1987 | Blanton . |
| D. 318,922 | 8/1991 | Kinder . |
| 1,673,622 | 6/1928 | Engalitcheff . |
| 2,560,199 | 7/1951 | Trichel et al. . |
| 2,801,424 | 8/1957 | Mercer . |
| 3,161,891 | 12/1964 | Bauman . |
| 3,400,409 | 9/1968 | James . |
| 3,495,278 | 2/1970 | Peters . |
| 3,540,433 | 11/1970 | Brockman . |
| 3,571,817 | 3/1971 | Gosnell . |
| 3,588,921 | 6/1971 | Nagel . |
| 3,625,654 | 12/1971 | Van Duyne . |
| 3,629,873 | 12/1971 | Long . |
| 3,654,638 | 4/1972 | Nye . |
| 3,775,777 | 12/1973 | Roberts, Jr. . |
| 4,137,573 | 2/1979 | Kroeger . |
| 4,203,169 | 5/1980 | Dale . |
| 4,276,889 * | 7/1981 | Kuntz et al. .......................... 4/301 X |
| 4,309,782 | 1/1982 | Paulin . |
| 4,408,905 * | 10/1983 | Ehrenkranz ....................... 4/144.1 X |
| 4,450,595 | 5/1984 | Saccomanno . |
| 4,466,445 | 8/1984 | Abrams . |
| 4,521,520 | 6/1985 | Jacke . |
| 4,554,687 * | 11/1985 | Carter et al. .......................... 4/144.2 |
| 4,569,090 | 2/1986 | Muller . |
| 4,932,083 | 6/1990 | Arozena . |
| 5,060,317 | 10/1991 | Bertelsen . |
| 5,671,485 | 9/1997 | Middlestead . |
| 5,956,782 | 9/1999 | Olguin . |

* cited by examiner

Primary Examiner—Robert M. Fetsuga
(74) Attorney, Agent, or Firm—Chase & Yakimo, L.C.

(57) ABSTRACT

A urine collection kit includes a flexible mounting strip positioned atop the toilet bowl rim for clamping thereto by the toilet seat. A plastic bag is attached to the mounting strip and depends into the toilet bowl upon strip clamping. Urine flow is directed towards a collection cup releasably seated within a port in the bottom of the bag. Adjacent the port are a plurality of slots and a second discharge port for passage of urine overflow therethrough to preclude urine back splash onto a seated patient. The second discharge port includes a tube depending below the cup to preclude urine flow thereon. The front portion of the bag includes additional slots allowing for a collapsed storage position.

20 Claims, 2 Drawing Sheets

URINE COLLECTION KIT

BACKGROUND OF THE INVENTION

This invention relates to a urine collection kit and, more particularly, to a kit which diminishes undesirable contact of voided urine onto a seated patient.

Past devices have been proposed to collect a urine sample from a patient. The collection of urine samples, as shown in the cited references, has been a problem for female patients. In turn, handheld devices or devices attached to the toilet bowl have been proposed to assist the patient in providing a urine sample. These devices have been relatively expensive to manufacture and not adaptable for easy coupling with toilet bowls of various configurations. Moreover, such past devices did not positively address the need to avoid the possibility of voided urine back splash/backup onto the seated patient. In the latter situation, the voided urine may overflow the collection cup which makes removal of the collection cup and disposal of the kit a problem.

SUMMARY OF THE INVENTION

In response thereto we have invented a urine collection kit which includes a flexible mounting strip adapted to fit atop toilet bowl rims of various configurations. Depending from the strip is a flexible collection trough in the form of a plastic bag having a discharge port preferably at the lowest distended portion of the bag. A collection cup is releasably seated within the primary discharge port. Slots in the collection trough adjacent the primary port allow for discharge of urine backup, relative to the collection, into the toilet bowl. Additionally, a second overflow port adjacent the primary port further directs any urine backup/overflow into the toilet bowl therebelow. A depending tube extending from this second overflow port further directs the urine overflow away from the depending collection cup. The discharge ports and/or overflow slots diminish undesirable back splash of the voided urine onto the seated patient as well as onto a handle of the collection cup. Furthermore, significant urine does not collect in the trough which enhances a hygienic disposal of the entire kit.

It is therefore a general object of this invention to provide a urine collection kit which is releasably connected to toilet bowls of various configurations and diminishes the backup and/or back splash and/or undesirable pooling of voided urine.

Another object of this invention is to provide a urine collection kit, as aforesaid, having a mounting strip adapted to be clamped between the toilet bowl rim and toilet seat.

A still further object of this invention is to provide a urine collection kit, as aforesaid, having a depending collection trough with releasable collection cup attached thereto.

A further object of this invention is to provide a urine collect ion kit, as aforesaid, having slots in the collection trough for discharge of a urine overflow therethrough.

Still another object of this invention is to provide a urine collection kit, as aforesaid, having an overflow port with depending tube in the collection trough for discharge of urine overflow therethrough and away from the urine collection cup.

A still further object of this invention is to provide a urine collection kit, as aforesaid, wherein the kit is easy to manufacture, store, transport, use and dispose.

Other objects and advantages of this invention will become apparent from the following description taken in connection with the accompanying drawings, wherein is set forth by way of illustration and example, a now preferred embodiment of this invention.

DESCRIPTION OF THE PREFERRED EMBODIMENT

Figure 1:
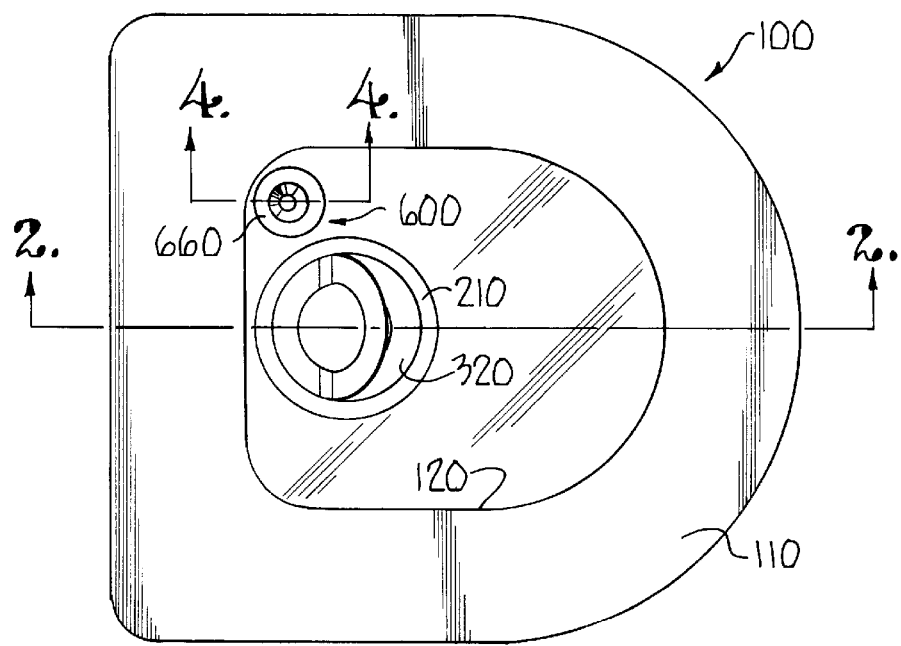
FIG. 1 is a top view of the kit.
Figure 2:
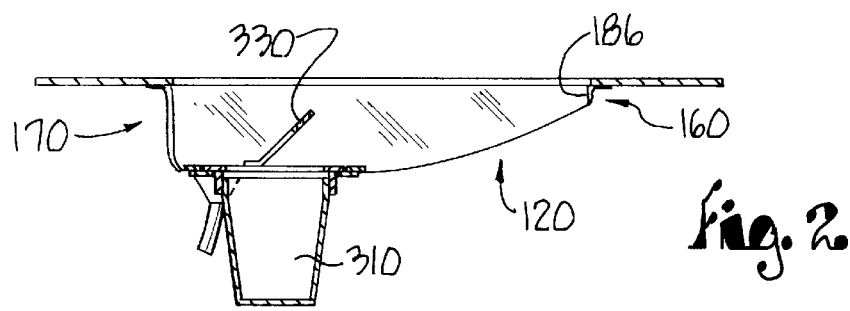
FIG. 2 is an elevation view of the kit taken along line 2—2 in FIG. 1.

Turning more particularly to the drawings, FIGS. 1–5 show the kit 100 as comprising a flexible mounting strip 110 having an annular configuration tracing the configuration of the toilet bowl rim 810. The annular strip 110 presents an opening 120 of a reduced configuration relative to the opening encompassed by the toilet rim 810.

Depending from the strip 110 is a flexible plastic bag 120 having front 160 and rear 170 ends which functions as a urine collection trough. The bag 120 includes a rim 122 attached to the underside of strip 110. The bag rim 122 surrounds a central bag opening in communication with opening 120 surrounded by the strip 110.

Within the bag is a primary exhaust port 200 preferably located at the lowest point of the distended bag and towards the rear 170 thereof. Port 200 has a reinforcing collar 210 therearound.

Figure 3:
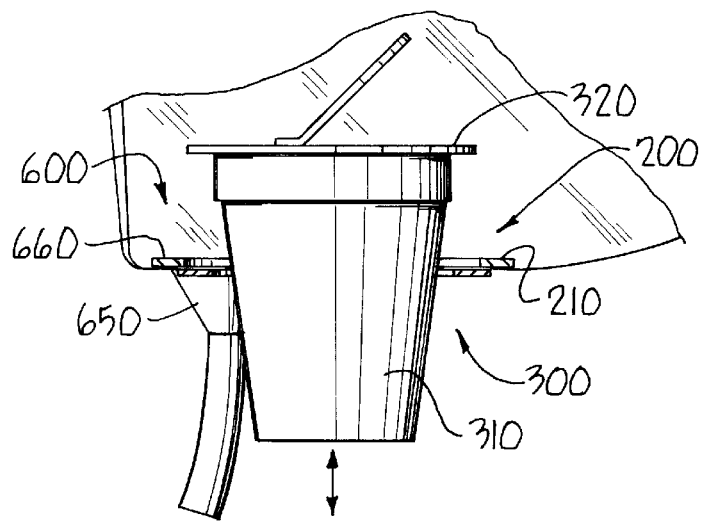
FIG. 3 is an enlarged fragmentary view of the collection cup prior to seating into the primary discharge port of the kit.
Figure 4:
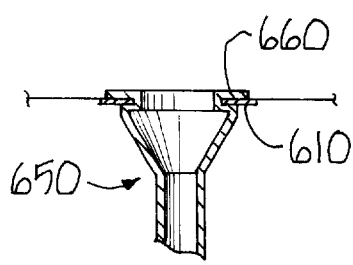
FIG. 4 is a fragmentary view, taken along lines 4—4 in FIG. 1, showing a portion of the overflow tube seated in the overflow port.
Figure 5:
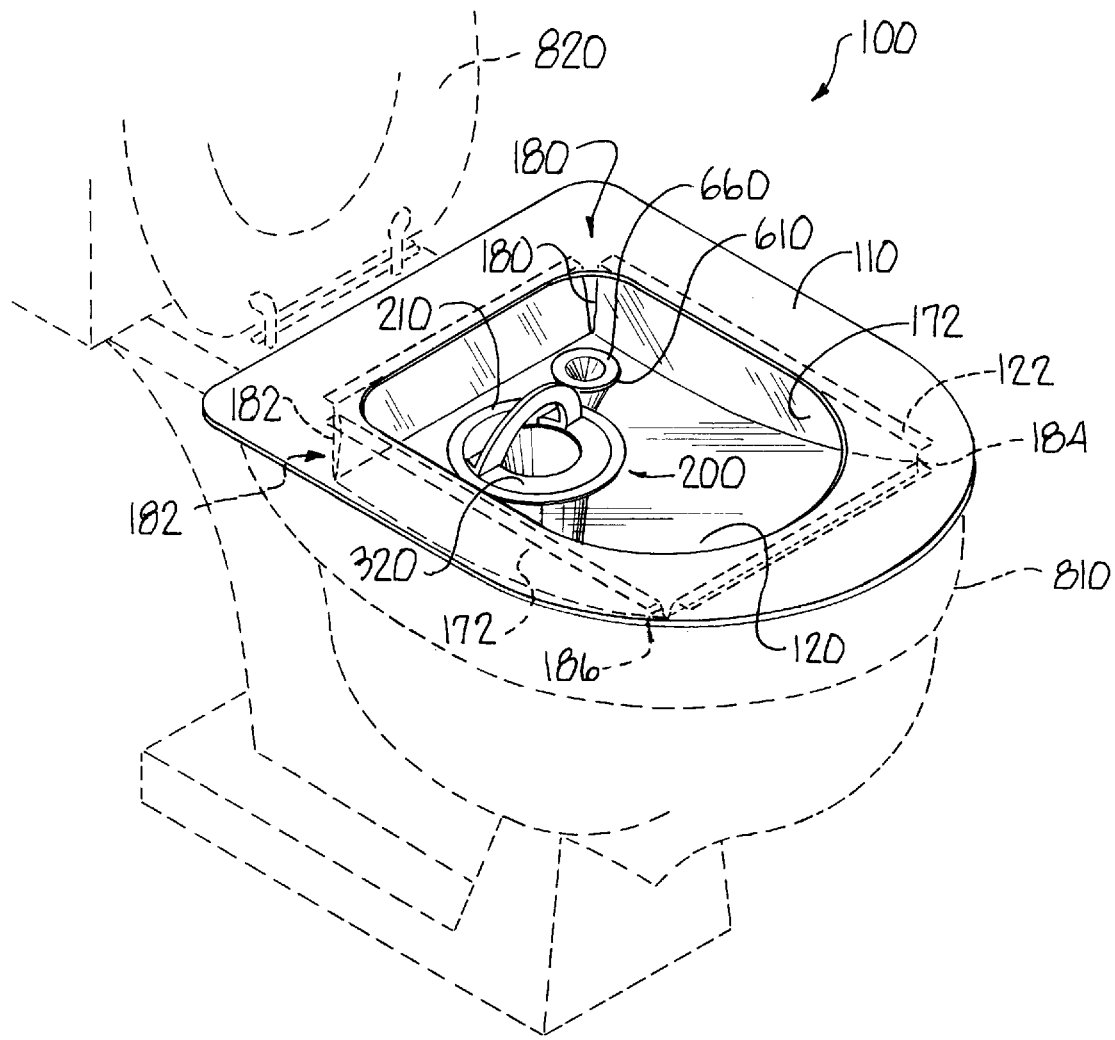
FIG. 5 is a perspective view showing the kit positioned relative to the toilet bowl prior to the upright toilet seat being moved to the horizontal kit clamping position atop the toilet bowl rim.

Port 200 is configured to releasably seat a urine collection cup 300 therein as shown in FIG. 3. The cup 300 includes a housing 310 with a support collar 320 at the top thereof. Extending from the collar 320 is a flexible handle 330 which may be flexed away from the primary urine stream. The cup 300 is easily seated within the primary discharge port 200 such that collar 320 lies atop collar 210. Alternatively, collar 210 may have a recess therein so as to recede the cup collar 320 into a flush relationship therebetween. Further adjacent port 200 is a second discharge port 600 with collar 610 to receive an overflow tube 650 with collar 660 therein. Tube 650 preferably depends below the bottom of the cup 300.

Adjacent to port 200 in the back wall 170 of the back 120 is a pair of spaced-apart slots 180, 182. Slots 180, 182 are adjacent the primary discharge port 200 and function to direct back splash of voided urine therethrough into the toilet bowl proper which does not flow into port 200 or port 600. Slots 184, 186 at the front 160 of the bag 120 allow the bag to be collapsed in a flat position to enhance storage and/or transport of the entire kit 100.

In use the strip 110 is clamped between the toilet bowl rim 810 and toilet seat 820 with the bag 120 depending into the toilet bowl proper. A seated patient may then void a urine sample. The configuration of the bag 120 directs the voided urine to the discharge port 200 and into the cup 300 seated therein. This urine flow may be enhanced by sloping the end walls 160, 170 and/or side walls 172 therebetween. An urine backup/overflow will be directed towards the adjacent slots 180, 182 and/or the overflow tube 650. This combination diminishes the possibility of any contact of the voided urine onto the seated user.

Cup 300 may then be removed by handle 330 and secured with lid for further transport and testing. The entire urine kit 100 may then be removed by the clamping strip 110 for collapse and subsequent disposal.

We have found that the use of the above kit 100 diminishes, if not precludes, the problems associated with providing a urine sample. The patients need not handle the collection device while providing the urine sample and need not worry about any urine overflow, back splash or the like.

It is to be understood that while a certain form of this invention has been illustrated and described, it is not limited thereto except insofar as such limitations are included in the following claims and allowable functional equivalents thereof.

Having thus described the invention, what is claimed as new and desired to be secured by Letters Patent is:

1. A urine collection kit for use with a toilet bowl having a rim and seat atop the rim comprising:

a flexible strip having a configuration adapted to mount atop the toilet bowl rim, said strip adapted for clamping between the toilet seat and rim;

a bag presenting an opening, said bag mounted to an underside of said strip, said clamped strip depending said bag into the toilet bowl;

a first aperture in said bag, said aperture at a position adapted for receipt of voided urine therethrough;

a cup for seating within said first aperture, said cup including an opening adapted for receipt of urine flow directed to said first bag aperture;

at least one slot in said bag positioned at a location adjacent said first aperture, said at least one slot adapted for passage of voided urine therethrough bypassing said first bag aperture.

2. The device as claimed in claim 1 wherein said at least one slot comprises at least a pair of spaced-apart slots in said bag on opposed sides of said aperture.

3. The device as claimed in claim 1 further comprising a second aperture in said bag adjacent said first bag aperture, said second bag aperture adapted for passage of voided urine therethrough bypassing said first bag aperture or said at least one slot.

4. The device as claimed in claim 3 further comprising a tube extending from said second bag aperture for directing urine into the toilet bowl therebelow.

5. The device as claimed in claim 4 wherein said tube includes a discharge end displaced below said cup to preclude urine flow thereon.

6. The device as claimed in claim 1 wherein said bag includes a first end portion adjacent a rear of the toilet bowl and a second end portion adjacent a front of the toilet bowl, said at least one slot positioned in said first end portion.

7. The device as claimed in claim 6 further comprising a slot in said second end portion of said bag to assist a collapse of said bag.

8. The device as claimed in claim 6 wherein said first bag aperture is adjacent said first bag end portion.

9. The device as claimed in claim 6 wherein said bag includes a bottom portion between said first and second bag end portions, said first bag aperture in said bag bottom portion.

10. The device as claimed in claim 9 wherein said bottom portion slopes between said first and second bag end portions.

11. A urine collection kit for use with a toilet bowl having a rim and seat comprising:

a rim adapted to be positioned atop the toilet bowl rim, said rim adapted for clamping between the toilet bowl rim and the toilet seat;

a bag connected to said kit rim and presenting an opening, said clamped kit rim depending said bag into the toilet bowl;

an aperture in said bag;

a cup seated in said bag aperture and presenting an opening for receipt of an urine flow therein, said bag configured to direct the voided urine towards said bag aperture;

means in said bag adjacent said bag aperture for passage of an overflow of the urine flow therethrough.

12. The device as claimed in claim 11 wherein said passage means comprises at least one slot in said bag upstream of said bag aperture for passage of the urine overflow thereto.

13. The device as claimed in claim 11 wherein said passage means further comprises a second aperture in said bag adjacent said bag aperture for passage of the urine overflow thereto.

14. The device as claimed in claim 12 wherein said passage means comprises a second aperture in said bag adjacent said bag aperture for passage of the urine overflow thereto.

15. The device as claimed in claim 13 further comprising a tube extending from said second aperture for directing the urine overflow into the toilet bowl therebelow.

16. A urine collection kit for use within an interior of a toilet bowl having a rim and seat, the rim comprising:

a bag presenting an opening, said bag having a first end portion and a second end position with a sloping bottom portion therebetween;

means for mounting said bag in a depending position within an interior of the toilet bowl with said first end portion adjacent a rear of the toilet bowl and said second end portion adjacent a front of the toilet bowl;

a first aperture in said bag bottom portion, said first aperture adjacent said first end portion for flow of voided urine therethrough;

a collection cup seated within said bag first aperture for receipt of the voided urine flow therein;

at least one second aperture in said first end portion, said at least one second aperture adapted for passage of a portion of the voided urine flow therethrough diverted from said first aperture.

17. The device as claimed in claim 16 further comprising a third aperture in said bag bottom portion, said third aperture adapted for passage of a portion of the voided urine flow therethrough diverted from said first and second apertures.

18. The device as claimed in claim 16 wherein said at least one second aperture comprises at least one slot in said first end portion upstream of said first aperture.

19. The device as claimed in claim 17 further comprising a tube depending from said third aperture for directing the urine flow away from said cup.

20. The device as claimed in claim 16 wherein said bottom portion downwardly slopes between said second and first end portions.

* * * * *